United States Patent
Bhagalia et al.

(10) Patent No.: US 10,403,006 B2
(45) Date of Patent: Sep. 3, 2019

(54) GUIDED FILTER FOR MULTIPLE LEVEL ENERGY COMPUTED TOMOGRAPHY (CT)

(71) Applicant: GENERAL ELECTRIC COMPANY, Schenectady, NY (US)

(72) Inventors: Roshni Bhagalia, Niskayuna, NY (US); Debashish Pal, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 119 days.

(21) Appl. No.: 15/248,119

(22) Filed: Aug. 26, 2016

(65) Prior Publication Data

US 2018/0061088 A1    Mar. 1, 2018

(51) Int. Cl.
G06T 11/00 (2006.01)
G06T 5/00 (2006.01)
A61B 6/03 (2006.01)
A61B 6/00 (2006.01)
G06T 5/50 (2006.01)

(52) U.S. Cl.
CPC ............ *G06T 11/003* (2013.01); *A61B 6/032* (2013.01); *A61B 6/482* (2013.01); *A61B 6/5258* (2013.01); *G06T 5/002* (2013.01); *G06T 5/50* (2013.01); *G06T 11/005* (2013.01); *A61B 6/481* (2013.01); *A61B 6/582* (2013.01); *G06T 2207/10081* (2013.01); *G06T 2207/10116* (2013.01); *G06T 2207/10144* (2013.01); *G06T 2211/408* (2013.01)

(58) Field of Classification Search
CPC ............... G06T 11/003; G06T 5/002; G06T 2207/10081; G06T 11/005; G06T 5/50; G06T 2211/408; G06T 2207/10144; G06T 2207/10116; A61B 6/481; A61B 6/482; A61B 6/5258; A61B 6/032; A61B 6/582
See application file for complete search history.

(56) References Cited

U.S. PATENT DOCUMENTS

| 5,966,678 | A | 10/1999 | Lam |
| 7,076,093 | B2 | 7/2006 | Lee et al. |
| 8,396,273 | B2 * | 3/2013 | Li .................... G06T 11/008 382/130 |

(Continued)

OTHER PUBLICATIONS

Zargar et al., "Role of filtering techniques in computed tomography (ct) image reconstruction", vol. 04, Issue: 12, pp. 69-74, Oct. 2015.

(Continued)

*Primary Examiner* — Yon J Couso
(74) *Attorney, Agent, or Firm* — Fletcher Yoder, P.C.

(57) ABSTRACT

As set forth herein low energy signal data and high energy signal data can be acquired. A first material decomposed (MD) image of a first material basis and a second material decomposed (MD) image of a second material basis can be obtained using the low energy signal data and the high energy signal data. At least one of the first or second MD image can be input into a guide filter for output of at least one noise reduced and cross-contamination reduced image. A computed tomography (CT) imaging system can be provided that includes an X-ray source and a detector having a plurality of detector elements that detect X-ray beams emitted from the X-ray source. Low energy signal data and high energy signal data can be acquired using the detector.

7 Claims, 2 Drawing Sheets

(56) References Cited

U.S. PATENT DOCUMENTS

| | | |
|---|---|---|
| 8,401,266 B2 | 3/2013 | Ku et al. |
| 8,682,087 B2 | 3/2014 | Tian |
| 9,241,093 B2 | 1/2016 | Gong et al. |
| 2003/0215120 A1* | 11/2003 | Uppaluri ............... A61B 6/482 382/128 |
| 2006/0109949 A1* | 5/2006 | Tkaczyk ............... A61B 6/032 378/4 |
| 2011/0150183 A1* | 6/2011 | Wu ....................... A61B 6/032 378/98.9 |
| 2017/0186194 A1* | 6/2017 | Koehler ............... G06T 11/008 |
| 2017/0206635 A1* | 7/2017 | Yu ............................ G06K 9/52 |

OTHER PUBLICATIONS

Devi S et al., "Image Enhancement Using Guided Image Filter and Wavelet Based Edge Detection", vol. 3, Issue: 3, pp. 1702-1706, May-Jun. 2012.

Goyal et al., "Image Enhancement using Guided Image Filter Technique", vol. 1, Issue: 5, pp. 213-217, Jun. 2012.

He, K., et al., "Guided Image Filtering," IEEE Transactions on Pattern Analysis and Machine Intelligence, vol. 35, Issue 6, pp. 1397-1409 (Jun. 2013).

\* cited by examiner

GUIDED FILTER FOR MULTIPLE LEVEL ENERGY COMPUTED TOMOGRAPHY (CT)

The subject matter disclosed herein relates to non-invasive imaging and, in particular, to the use of dual energy imaging.

BACKGROUND

In the fields of medical imaging and security screening, non-invasive imaging techniques have gained importance due to benefits that include unobtrusiveness, convenience, and speed. In medical and research contexts, non-invasive imaging techniques are used to image organs or tissues beneath the surface of the skin. Similarly, in industrial or quality control (QC) contexts, non-invasive imaging techniques are used to examine parts or items for hidden defects that may not be evident from an external examination. In security screening, non-invasive imaging techniques are typically used to examine the contents of containers (e.g., packages, bags, or luggage) without opening the containers and/or to screen individuals entering or leaving a secure location.

A number of non-invasive imaging modalities exist today. One such technique, dual energy (DE) radiography, involves the acquisition of two X-ray images at different energies within a relatively small time interval. The two images are then used to decompose the imaged anatomy and create a first image of a first material (e.g., water) and a second image of a second material (e.g., iodine). While such materially decomposed images contain clinically pertinent information, they typically result in a lower signal to noise ratio (SNR) than conventional computed tomography images.

Existing techniques that attempt to increase the signal in such images are often accompanied by undesired radiation dosages. Accordingly, a variety of techniques have been developed that attempt to reduce the noise in the reconstructed images. However, such techniques have fallen short of reducing the noise to acceptable levels. In addition, many noise reduction techniques eliminate noise while introducing undesirable artifacts that contaminate the materially decomposed images. One problem noted with current DE image reconstruction methods is cross contamination (CC). In a cross-contaminated image, some parts of a first material can be represented as a second material and some parts of a second material can be represented as a first material. Accordingly, techniques are needed to overcome the problems associated with DE image reconstruction. The techniques described herein are intended to address one or more of these problems associated with DE imaging systems.

In medical imaging it is common to use a contrast agent for visualization of various body tissues. A contrast agent is a substance used to enhance contrast of some structures or fluids within a body subject to medical imaging. Iodine based contrast agents are commonly used.

BRIEF DESCRIPTION

As set forth herein low energy signal data and high energy signal data can be acquired. A first material decomposed (MD) image of a first material basis and a second material decomposed (MD) image of a second material basis can be obtained using the low energy signal data and the high energy signal data. At least one of the first MD image or the second MD image can be input into a guide filter for output of at least one noise reduced and cross-contamination reduced image. A computed tomography (CT) imaging system can be provided that includes an X-ray source and a detector having a plurality of detector elements that detect X-ray beams emitted from the X-ray source. Low energy signal data and high energy signal data can be acquired using the detector.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As set forth herein low energy signal data and high energy signal data can be acquired. A first material decomposed (MD) image of a first material basis and a second material decomposed (MD) image of a second material basis can be obtained using the low energy signal data and the high energy signal data. The first MD image can be input into a guide filter for output of at least one noise reduced and cross-contamination reduced image. A computed tomography (CT) imaging system can be provided that includes an X-ray source and a detector having a plurality of detector elements that detect X-ray beams emitted from the X-ray source. Low energy signal data and high energy signal data can be acquired using the detector.

Figure 1:
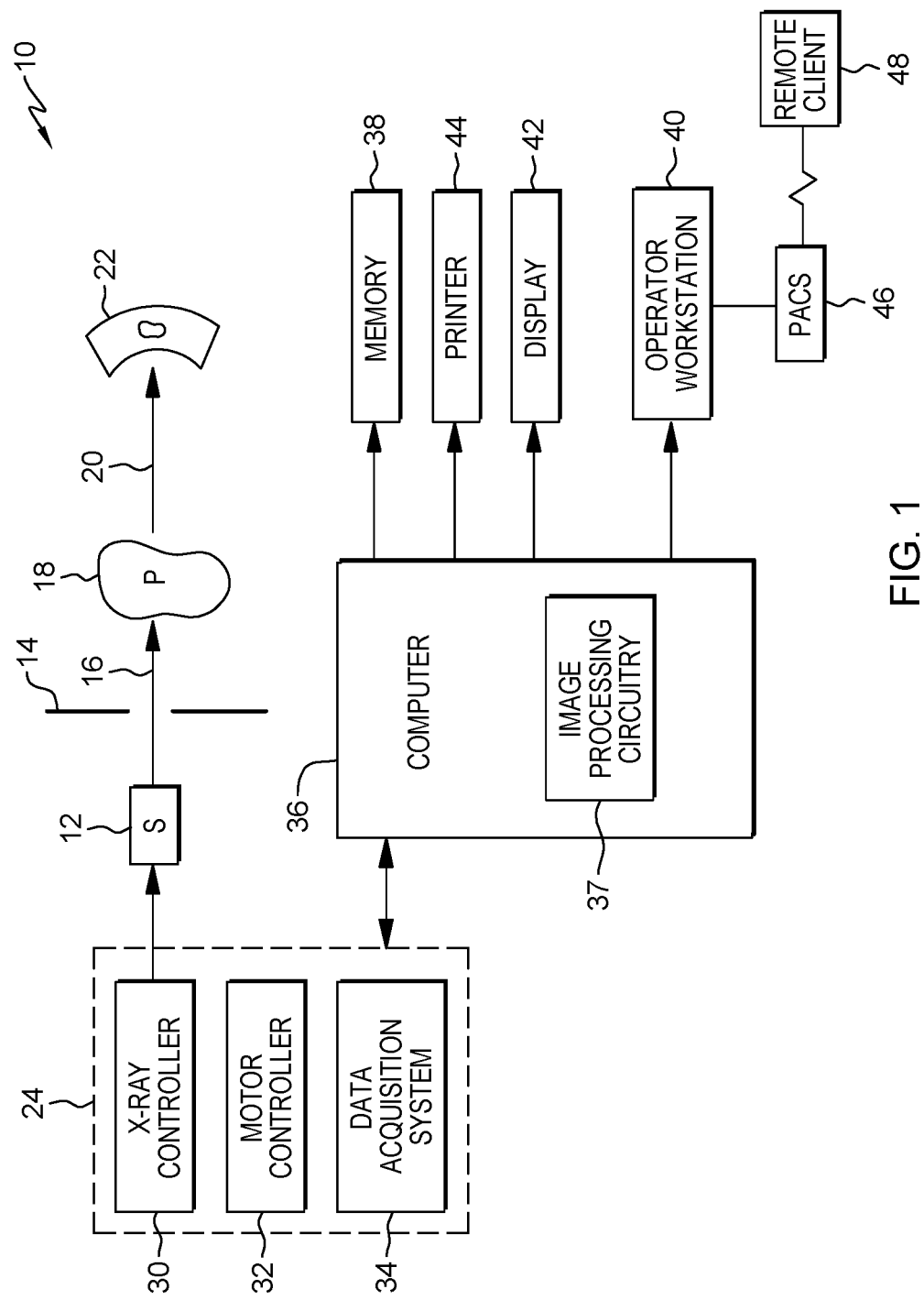
FIG. 1 is a perspective view of a dual energy (DE) X-ray imaging system in accordance with an embodiment of the present technique.

Turning now to the drawings, FIG. 1 illustrates a multi-energy X-ray imaging system provided by dual-energy X-ray imaging system 10. In the illustrated embodiment, the dual-energy X-ray imaging system 10 is a digital X-ray system that is designed to both acquire and process image data for display in accordance with the present techniques. The system 10 can be capable of acquiring dual-energy digital X-ray images. In other words, the system 10 is capable of acquiring projection data of a region of interest using X-rays having a first energy level (e.g., low energy) and then acquiring projection data of the region of interest using X-rays having a second, different energy level (e.g., high energy). Furthermore, the dual-energy X-ray imaging system 10 can be capable of producing separate images of different basis materials (e.g., bone, water, and so forth) using the X-rays of differing energy levels. That is, the first basis material and the second basis material can have different absorption characteristics for the low energy X-rays and the high energy X-rays, enabling the system 10 to distinguish the absorption of X-rays caused by the first basis material and the absorption caused by the second basis material.

Such features allow the system 10 to be operable to produce both low energy projections and high energy projections, which can be decomposed (based on these differential absorption characteristics) to produce basis pair material images (e.g., water and bone, water and iodine, iodine and calcium, etc.) for further analysis of the desired anatomy. Furthermore, though the illustrated imaging system 10 is discussed in the context of medical imaging, the techniques and configurations discussed herein are applicable in other non-invasive imaging contexts, such as security screening or industrial nondestructive evaluation of manufactured parts.

It should be noted that although such a dual-energy system is described in the foregoing description, the concepts are equally applicable to any multi-energy system (e.g., any system operating at more than two energy levels) as well. Furthermore various methodologies can be used in practice for generating signal data at different energy levels. For example, the system 10 can acquire projection data at a variety of angular positions. With the system 10 in each position, signal data at both energy levels (low energy signal data and high energy signal data) can be acquired, or the various positions can be traversed to acquire signal data at one energy level (e.g. low energy signal data), and then the same positions can be repeated to acquire signal data at the second energy level (e.g. high energy signal data). Still further, if the system includes a detector capable of acquiring signal data at two different energy levels simultaneously, combined acquisition at the energy levels can be performed. Again, embodiments of the present technique can be used in conjunction with any such system that can be configured to allow the separation of basis materials into separate images.

In the embodiment illustrated in FIG. 1, the CT imaging system 10 includes an X-ray source 12. The source 12 can be positioned proximate to a collimator 14. The collimator 14 can consist of one or more collimating regions, such as lead or tungsten shutters, for each emission point of the source 12. The collimator 14 typically defines the size and shape of the one or more X-ray beams 16 that pass into a region in which a subject 18, such as a human patient, is positioned. Each X-ray beam 16 can be generally fan-shaped or cone-shaped, depending on the configuration of the detector and/or the desired method of data acquisition, as discussed below. An attenuated portion 20 of each X-ray beam 16 passes through the subject 18 and impacts a detector represented generally at reference numeral 22.

The illustrated system 10 can include one or more collimators 14 or filters that shape or limit an emitted stream of radiation directed toward a region in which the subject 18 is positioned. However, in some embodiments, the system 10 may not include a collimator, and images can be obtained using the full field of view of the system 10. Alternatively, in certain embodiments, the field of view of the system 10 can be reduced by using the collimator 14 to reduce the spread of X-rays produced by the X-ray source 12. The collimator 14 can be selectively placed over the X-ray source 12 when desired or the collimator 14 can be kept disposed over the X-ray source 12. Additionally, the collimator 14 can be adjustable so that full (or wide) field of view and reduced (or narrow) field of view images can be obtained with the collimator disposed over the X-ray source 12. It should be noted that the present techniques can be used in an imaging system having a standard collimator, a slit collimator, any other suitable collimator, or no collimator at all.

The detector 22 can be formed by a plurality of detector elements that detect the X-ray beams 16 after they pass through or around the subject 18. Each detector element produces an electrical signal that represents the intensity of the X-ray beam 16 incident at the position of the detector element when the beam strikes the detector 22. Detector 22 having a plurality of detector elements can be referred to as a detector array. Alternatively, each element of detector 22 can count incident photons in the X-ray beam 16 and can also determine their energy. Typically, the X-ray beam 16 is generated and the corresponding electrical signals are acquired at a variety of angular positions around the subject of interest so that a plurality of radiographic projection views can be collected. The electrical signals can be acquired and processed to reconstruct an image that is indicative of the features within the subject 18, as discussed in further detail below.

It should be noted that the digital X-ray detector 22 can be any detector that is operable to perform multi-energy e.g. dual-energy X-ray imaging. For instance, the digital X-ray detector 22 can be an amorphous silicon flat panel that has the ability to acquire two images in rapid succession. Additionally, the detector 22 can include energy discriminative detector materials that are capable of separating X-ray photons from one acquisition into two energy bins. Such detectors can be useful in acquiring data via energy discrimination or photon counting approaches. That is, the digital detector 22 can be capable of facilitating image acquisition speeds that enable the acquisition of low and high energy signal data with large energy separation (mean energy separations in spectra as great as approximately 90 keV or greater), which can translate to improved image subtraction. In one embodiment, the X-ray detector 22 converts the X-ray photons received on its surface to lower energy photons, and subsequently to electric signals, which are acquired and processed to reconstruct one or more images of the features within the subject.

A system controller 24 commands operation of the imaging system 10 to execute examination protocols and to process the acquired data. The source 12 is typically controlled by the system controller 24. Generally, the system controller 24 furnishes power, focal spot location, control signals and so forth, for the CT examination sequences. The detector 22 is coupled to the system controller 24, which commands acquisition of the signals generated by the detector 22. The system controller 24 can also execute various signal processing and filtration functions, such as initial adjustment of dynamic ranges, interleaving of digital image data, and so forth. In the present context, system controller 24 can also include signal-processing circuitry and associated memory circuitry. As discussed in greater detail below, the associated memory circuitry can store programs and/or routines executed by the system controller 24 or a processor-based system in communication with the system controller 24, such as programs or routines for implementing the presently disclosed techniques. Further, the memory circuitry of the system controller 24 can also store configuration parameters, image data, and so forth. In one embodiment, the system controller 24 can be implemented as all or part of a processor-based system such as a general purpose or application-specific computer system.

In the illustrated embodiment of FIG. 1, the system controller 24 can control the movement of a linear positioning subsystem and a rotational subsystem via a motor controller 32. In an embodiment where the imaging system 10 includes rotation of the source 12 and/or the detector 22, the rotational subsystem 26 can rotate the source 12, the collimator 14, and/or the detector 22 about the subject 18. It should be noted that the rotational subsystem 26 might include a gantry comprising both stationary components (stator) and rotating components (rotor). The linear positioning subsystem can enable the subject 18, or more specifically a patient table that supports the subject 18, to be displaced linearly. Thus, the patient table can be linearly moved within the gantry or within an imaging volume (e.g., the volume located between the source 12 and the detector 22) and enable the acquisition of data from particular areas of the subject 18 and, thus the generation of images associated with those particular areas. Additionally, the linear positioning subsystem 28 can displace the one or more components of the collimator 14, so as to adjust the shape and/or direction of the X-ray beam 16. In embodiments comprising a stationary source 12 and a stationary detector 22, a mechanical rotational subsystem can be absent, with emitters spaced at different angular locations about the subject instead being activated at different times to allow acquisition of projections at different angles. Similarly, in embodiments in which the source 12 and the detector 22 are configured to provide extended or sufficient coverage along the z-axis (i.e., the axis associated with the main length of the subject 18) and/or linear motion of the subject is not required, the linear positioning subsystem 28 can be absent.

The source 12 can be controlled by an X-ray controller 30 disposed within the system controller 24. The X-ray controller 30 can be configured to provide power and timing signals to the source 12. In addition, in some embodiments the X-ray controller 30 can be configured to selectively activate the source 12 such that tubes or emitters at different locations within the system 10 can be operated in synchrony with one another or independent of one another.

Further, the system controller 24 can comprise a data acquisition system 34. In such an embodiment, the detector 22 can be coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36. Alternatively, in other embodiments, the detector 22 can convert the sampled analog signals to digital signals prior to transmission to the data acquisition system 34.

In the depicted embodiment, a computer 36 can be coupled to the system controller 24. The data collected by the data acquisition system 34 can be transmitted to the computer 36 for subsequent processing and reconstruction. For example, the data collected from the detector 22 can undergo pre-processing and calibration at the data acquisition system 34 and/or the computer 36 to produce representations of the line integrals of the attenuation coefficients of the subject 18 and the scanned objects. In one embodiment, the computer 36 contains image-processing circuitry 37 for processing and filtering the data collected from the detector 22. The processed data, commonly called projections, can then be reconstructed by the image processing circuitry 37 to form an image of the subject 18 and/or the scanned area. A projection as set forth herein in one embodiment can include a set of line integrals of attenuation coefficients for a subject being imaged. Projections can be obtained for each of several angles.

In one implementation, the projections can be reconstructed into noise reduced materially decomposed (MD) images, such as in accordance with the techniques discussed herein. For example, the image processing circuitry 37 can include instructions for receiving acquired image data, removing noise from the digital data in accordance with the techniques described in detail below, and outputting via an output device, such as the display 42 or printer 44 materially decomposed images that are noise reduced and cross contamination reduced. Once reconstructed, the image produced by the system 10 of FIG. 1 can reveal an internal region of interest of the subject 18 which can be used for diagnosis, evaluation, and so forth.

The computer 36 can comprise or communicate with a memory 38 that can store data processed by the computer 36, data to be processed by the computer 36, or routines and/or algorithms to be executed by the computer 36, such as for processing image data in accordance with the present techniques. It should be understood that any type of computer accessible memory device capable of storing the desired amount of data and/or code can be utilized by such a system 10. Moreover, the memory 38 can comprise one or more memory devices, such as magnetic, solid state, or optical devices, of similar or different types, which can be local and/or remote to the system 10. The memory 38 can store data, processing parameters, and/or computer programs comprising one or more routines or algorithms for performing the iterative reconstruction and/or the artifact correction processes described herein.

The computer 36 can also be adapted to control features enabled by the system controller 24 (i.e., scanning operations and data acquisition). Furthermore, the computer 36 can be configured to receive commands and scanning parameters from an operator via an operator workstation 40 which can be equipped with a keyboard and/or other input devices. An operator can, thereby, control the system 10 via the operator workstation 40. Thus, the operator can observe from the computer 36 the reconstructed image and other data relevant to the system 10, initiate imaging, select and apply image filters, and so forth. Further, the operator can manually identify and/or review features and regions of interest from the reconstructed image. Automated detection algorithms can be applied to aid in identifying and/or manipulating the features or regions of interest.

As illustrated, the system 10 can also include a display 42 coupled to the operator workstation 40. The display 42 can be utilized to observe the reconstructed images, for instance. Additionally, the system 10 can include a printer 44 coupled to the operator workstation 40 and configured to print a copy of the one or more reconstructed images. The display 42 and the printer 44 can also be connected to the computer 36 directly or via the operator workstation 40. Further, the operator workstation 40 can include or be coupled to a picture archiving and communications system (PACS) 46. It should be noted that PACS 46 might be coupled to a remote system 48, radiology department information system (RIS), hospital information system (HIS) or to an internal or external network, so that others at different locations can gain access to the image data.

Although only one operator workstation is depicted, one or more operator workstations 40 can be linked in the system 10 for outputting system parameters, requesting examinations, viewing images, and so forth. In general, displays 42, printers 44, workstations 40, and similar devices supplied within the system 10 can be local to the data acquisition components, or can be remote from these components, such as elsewhere within an institution or hospital, or in an entirely different location, linked to the imaging system 10 via one or more configurable networks, such as the Internet, virtual private networks, and so forth. Furthermore, although the previous discussion discloses typical embodiments of the imaging system 10, any other suitable system configuration can be employed to acquire image data and process such data via the techniques described herein.

Figure 2:
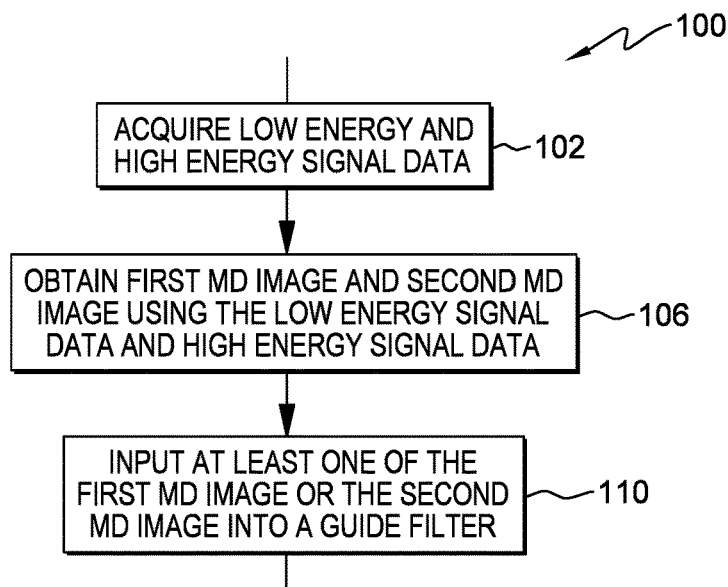
FIG. 2 is a flow diagram illustrating an imaging method.

With the foregoing system discussion in mind, FIG. 2 is a flow diagram of a dual energy imaging method 100 that can be used with a system such as that depicted in FIG. 1 to acquire and process digital X-ray and computed tomography (CT) data.

At block 102 low energy signal data and high energy signal data can be acquired. At block 106 a first material decomposed (MD) image of a first material basis and a second material decomposed (MD) image of a second material basis can be obtained using the low energy signal data and the high energy signal data. At block 110 the first MD image can be input into a guide filter to produce a noise reduced and cross-contamination reduced MD image.

In accordance with the depicted method of FIG. 2, low energy signal data and high energy signal data can be obtained at block 102. Although in the illustrated embodiment, the method 100 includes acquisition of data at only two energy levels, further embodiments can include data acquisition at any number of energy levels. Furthermore, the data acquisition can occur via any of a variety of dual or multiple energy protocols. For example, the data can be acquired in a rotate-rotate pattern in which a gantry on which the source 12 and detector 22 are disposed rotates one time for each energy level. In one embodiment, the imaging system can acquire data in any of a number of fast kV switching approaches in which the low and high energy data is acquired in an interleaved fashion, e.g., one low—one high, one low—two high, two low—two high, simultaneously, and so forth. Again, any process capable of acquiring data from at least two energy levels can be used in conjunction with the presently contemplated noise reduction techniques.

After acquiring the low energy signal data and high energy signal data, the method 100 can include obtaining at block 106 a first material decomposed (MD) image of a first material basis and a second material decomposed (MD) image of a second material basis can be obtained using the low energy signal data and the high energy signal data. The obtaining can include converting the low energy signal data to low energy projections and converting the high energy signal data to high energy projections. The low and high energy projections can be used to re-create a separate MD image for each material in a basis material pair. Such MD images typically include information regarding the material density of each of the basis materials and, thus, provide additional information that can be clinically useful. In one aspect due to e.g. hardware limitations of imaging system 10 including detector 22 significant noise can be present in MD images of a first basis material and a second basis material.

X-ray attenuation in the diagnostic energy range is mostly due to Compton effect (incoherent scattering) and photoelectric effect (absorption); these two effects can be viewed as linearly independent functions of energy. The mass attenuation coefficient $U/p$ (E) of any material can be expressed as a linear combination of these two basis functions to a good approximation and, further on, that alternatively the mass attenuation coefficient functions of any two materials, which differ sufficiently in their atomic number Z, can equally be used as basis functions.

For any arbitrary object, the line integral over the linear attenuation coefficient can be expressed as $$\int \mu(\vec{r},E)ds = (\mu/\rho)_1(E)\cdot\delta_1 + (\mu/\rho)_2(E)\cdot\delta_2 \quad \text{Equation 1}$$

with $$\delta_i = \int \rho_i(\vec{r})ds \; i=1,2. \quad \text{Equation 2}$$

Where $\delta_1$ represents the area density in g/cm2 and $p_i(r)$ is the local density in g/cm3 of basis material i. In dual energy methods, attenuation is measured for two different energies or X-ray spectra which yields two non-linear equations for each ray path $$I_h(\delta_1,\delta_2) = \int I_{0h}(E)\cdot e^{-(\mu/\rho)_1(E)\cdot\delta_1 - (\mu/\rho)_2(E)\cdot\delta_2}dE \quad \text{Equation 3}$$

$$I_l(\delta_1,\delta_2) = \int I_{0l}(E)\cdot e^{-(\mu/\rho)_1(E)\cdot\delta_1 - (\mu/\rho)_2(E)\cdot\delta_2}dE, \quad \text{Equation 4}$$

Where I and $I_0$ are the attenuated and primary intensities, respectively, the subscripts h and l refer to the high and low kV p spectra. The basis material decomposition method has to solve this pair of equations for the two unknown area densities $\delta_1$ and $\delta_2$ using appropriate calibration measurements or calculations. Attenuation values $S_h$, $S_l$ can be expressed as functions of intensity attenuated and primary values I and $I_0$. The above equations describe the transformation of a pair of attenuation values into a pair of density values $(S_h,S_l) \rightarrow (\delta_1, \delta_2)$. Material decomposition can include use of a set of equations for transforming attenuation values into density values.

Referring to block 110 method 100 can include inputting an MD image, e.g. having a set of density values, into a guide filter which can output a noise reduced and cross contamination reduced image. An MD filter can have first and second guide images. Each of the first and second guide images can be provided using the first MD image of the first basis material and the second MD image of the second basis material.

In dual energy CT, cross contamination (CC) is a bleed through of the signal of a first basis material image (e.g. water) and a second basis material image (e.g. iodine) or vice versa. According to embodiments herein there is derived and designed a filter to reduce CC and noise in basis material images.

Embodiments herein recognize that a raw MD image $p_1$ of basis material$_1$ can be expressed as follows $$p_1 = q_1 + n_1 \quad \text{Equation 5}$$

where $q_1$ is the noise-free signal of the raw MD image of basis material$_1$ and $n_1$ is the noise of the raw MD image.

A raw MD image $p_2$ of basis material$_2$ can be expressed as follows $$p_2 = q_2 + n_2 \quad \text{Equation 6}$$

where $q_2$ is the noise-free signal of the raw MD image of basis material$_2$ and $n_2$ is the noise of the raw MD image.

Embodiments herein also recognize that MD images can be mixed to provide images in different proportions of a first MD image and a second MD image. For example, $$I = p1 - \alpha p2 \quad \text{Equation 7}$$

$$J' = \beta p1 + p2 \quad \text{Equation 8(a)}$$

$$J = \text{De-noised}(J') \quad \text{Equation 8(b)}$$

where I is a mixed image combined by mixing $p_1$ and $p_2$ according to a first process wherein the mixing parameters are computed such that $n_1$ and $n_2$ cancel out and J' is a mixed image combined by mixing $p_1$ and $p_2$ according to a second process such that the noise values $n_1$ and $n_2$ are not canceled out, and then performing a de-noising procedure to remove the noise and produce image J. Resulting mixed images I and J can include different proportions of MD images of a first and second basis material. Resulting mixed images I and J can be regarded to be de-noised images but, by virtue of their combining MD images of different bases can be cross contaminated (CC) images. Given a CC-free but very noisy input basis material MD image $p(i) = p_1$ the desired unknown de-noised, CC-free image $q(i)$ can be estimated. Since the CC in I and J is spatially varying but locally smooth, q can be modeled by a local linear model:

$$q_k(i) = a_k I(i) + b_k J(i) + c_k; \forall i \in w_k \quad \text{Equation 9}$$

where $w_k$ is a small local window centered around location $x_i$ and I(i) and J(i) are the known CC water and CC iodine values at $x_i$ respectively.

According to Equation 9 an unknown noise free and cross contamination free image q(i) can be expressed as a local linear model wherein terms include a proportion of I, a de-noised and cross contaminated image, and a proportion of J, another de-noised and cross contaminated image. Equation 9 uses de-noised images with inaccurate proportions of basis materials to determine a de-noised image with an accurate representation of basis materials. The unknown coefficients $a_k$, $b_k$ and $c_k$ are constant over the local window $w_k$ and vary spatially as the window is shifted. Given I, J and $p=p_1$, q can be estimated by solving for the unknown coefficients in Equation 9 to reduce a non-decreasing function of the residual noise, $h(q(i)-p(i))$ which is differentiable with respect to (w.r.t.) the unknown coefficients, over the local windows $w_k$; k=1, 2 . . . K. Additional regularization constraints, $g1(a_k)$ and $g2(b_k)$, can also be included to mitigate abrupt spatial changes in the estimated coefficients. Mathematically this results in a cost function of the form:

$$E_k = \sum_{i \in w_k} h(q(i) - p(i)) + g1(a_k) + g2(b_k) \qquad \text{Equation 10}$$

$$E_k = \sum_{i \in w_k} (h(a_k I(i) + b_k J(i) + c_k - p(i)) + g1(a_k) + g2(b_k))$$

The unknown coefficients can then be determined by differentiating the above with respect to $a_k$, $b_k$ and $c_k$ and solving for the local minima by equating each of the partial derivatives $$\frac{\partial E_k}{\partial a_k}, \frac{\partial E_k}{\partial b_k} \text{ and } \frac{\partial E_k}{\partial c_k}$$

to zero. This in turn yields estimates for the unknown coefficients in terms of the known quantities, p, I and J, i.e.:

$$a_k = f1(p,I,J); b_k = f2(p,I,J); c_k = f3(p,I,J) \qquad \text{Equation 11}$$

Where the specific form of functions $f1(\cdot)$, $f2(\cdot)$ and $f3(\cdot)$ is completely determined by the forms of $h(\cdot)$, $g1(\cdot)$ and $g2(\cdot)$ in Equation 10. In one embodiment of the above, function $h(\cdot)$ can be the L2-norm of its argument, i.e. $h(x)=\|x^2\|$ and g1 and g2 can be scaled magnitude functions, i.e. $g_j(x)=\psi_j x^2$, j=1,2, where is $\psi_j$ a known fixed constant.

Equation 9 can be regarded as a guide filter with at least one of a first MD image $p_1$ or second MD image $p_2$ as an input and the images I(i) and J(i) as guide images. In the example of Equation 9 the guide filter can include a linear equation model in which a noise free cross contamination free image q is expressed as a linear equation having terms provided by a proportion of a first de-noised cross-contaminated image and a proportion of a second de-noised cross-contaminated image. The first de-noised cross contaminated image can be provided by a basis material$_1$ (e.g. water) image which can be referred to as a first guide image. The second de-noised cross contaminated image can be provided by a basis material$_2$ (e.g. iodine) image which can be referred to as a second guide image.

In one aspect a first guide image, I, can be provided by mixing a first MD image and second MD image using a first process. According to a first process for mixing first and second images, negatively correlated noise can be cancelled out and a cross contaminated image can be produced— where I is a mixed image combined by mixing $p_1$ and $p_2$ according to a first process wherein the mixing parameters are computed such that $n_1$ and $n_2$ cancel out and J' is a mixed image combined by mixing $p_1$ and $p_2$ according to a second process such that the noise values $n_1$ and $n_2$ are not canceled out, and then performing a de-noising procedure to remove the noise and produce image J.

In one aspect a second guide image, J, can be provided by mixing a first and second MD image according to a second process to produce a cross contaminated mixed image and then reducing the noise in the mixed image using a de-noising procedure. The second process can be differentiated from the first process. The second process can be a process in which noise is not cancelled by mixing of a first basis material MD image and a second basis material MD image. The second process can be a process in which noise of a first basis material MD image and a second basis material MD image is not canceled out.

Exemplary de-noising procedures for use in de-noising a mixed image provided by mixing a first basis material MD image and a second basis material MD image by a second process can include a variety of different technologies. Examples of de-noising procedures can include e.g. linear smoothing filter de-noising procedures (e.g. Gaussian or Laplacian smoothing), non-local means de-noising procedures, edge-preserving smoothing de-noising procedures, anisotropic diffusion de-noising procedures, bilateral filters de-noising procedure.

According to a Gaussian filter de-noising procedure, a Gaussian smoothing operator can be provided by a 2-D convolution operator, including a kernel representing a shape of a Gaussian, that is used to 'blur' images and remove detail and noise.

According to a Laplacian filter de-noising procedure, an algorithm to smooth a polygonal mesh can be provided. For each vertex in a mesh, a new position is chosen based on local information (such as the position of neighbors) and the vertex is moved there. In the case that a mesh is topologically a rectangular grid (that is, each internal vertex is connected to four neighbors) then this operation produces the Laplacian of the mesh.

According to a non-local means de-noising procedure a mean can be taken of all pixels in the image, weighted by how similar these pixels are to the target pixel. This results in much greater post-filtering clarity, and less loss of detail in the image compared with local mean algorithms.

According to edge-preserving smoothing de-noising procedure, textures can be removed from an image while retaining sharp edges. Examples are the bilateral filter, and anisotropic diffusion.

According to a bilateral filter de-noising procedure, an intensity value at each pixel in an image can be replaced by a weighted average of intensity values from nearby pixels. This weight can be based on a Gaussian distribution. In one embodiment, weights can depend not only on Euclidean distance of pixels, but also on the radiometric differences e.g. color intensity range differences, depth distance, etc. Sharp edges can be preserved by systematically looping through each pixel and adjusting weights to the adjacent pixels accordingly.

According to an anisotropic diffusion de-noising procedure, edges, lines or other details that are important for the interpretation of the image can be preserved while reducing noise. According to an anisotropic diffusion de-noising procedure an image can be used to generate a parameterized family of successively more and more blurred images based on a diffusion process. Each of the resulting images in the family of blurred images can be given as a convolution between the image and a 2D isotropic Gaussian filter, where the width of the filter increases with the parameter. A diffusion process can be a linear and space-invariant transformation of the original image. According to an anisotropic diffusion de-noising procedure a family of parameterized images can be generated, but each resulting image can be a combination between the original image and a filter that depends on local content of the original image. Anisotropic diffusion can be regarded to be a non-linear and space-variant transformation of an original image.

Figure 3:
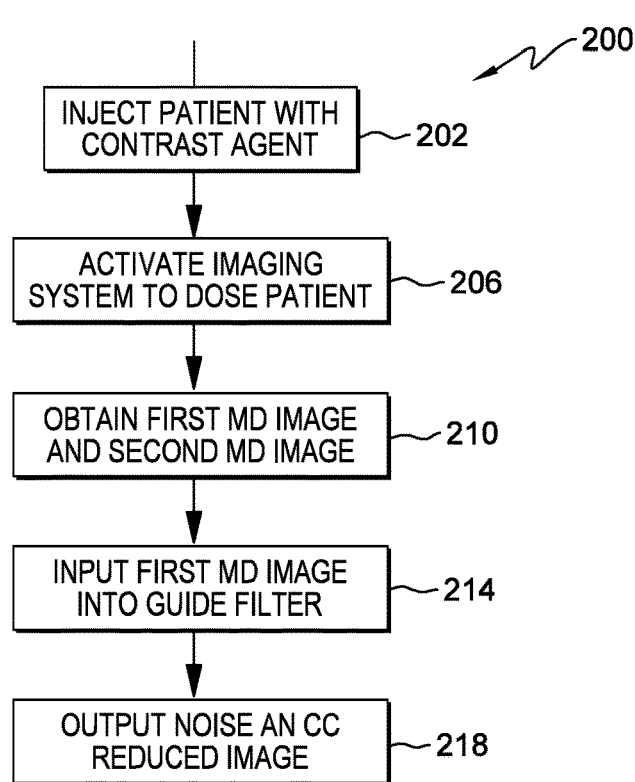
FIG. 3 is a flow diagram illustrating a method of using an imaging system.

A method 200 for imaging a patient is set forth in reference to FIG. 3. At block 202 a patient can be injected with a contrast agent, e.g. an iodine based contrast agent. In one aspect the injecting can be performed without prior dosing of a patient by activation of imaging system 10 to obtain high energy and low energy signal data. At block 206 imaging system 10 can be activated for acquiring low energy signal data and high energy signal data to subject a patient to a dose of radiation. Also at block 206 low energy signal data and high energy signal data can be acquired. At block 210 a first material decomposed (MD) image of a first material basis (e.g. water) and a second material decomposed (MD) image of a second material basis (e.g. iodine) can be obtained using the low energy signal data and the high energy signal data. At block 214 at least one of the first MD image or second MD image can be input into a guide filter for output of at least one noise reduced and cross-contamination reduced image. At block 218 the noise reduced and cross-contamination reduced image can be output to a display 42 of imaging system 10. If the basis material image pairs are chosen such that one basis corresponds to the contrast agent (e.g. iodine), then the noise-reduced and cross-contamination reduced MD image from block 218 can accurately depict what proportional of the signal can be attributed to contrast agent density. Thus it follows that this corrected MD image enables suppression of the contrast agent related signal in the original image at the output of block 210 by simple weighted subtraction.

This written description uses examples to disclose the invention, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Forms of term "based on" herein encompass relationships where an element is partially based on as well as relationships where an element is entirely based on. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

The invention claimed is:

1. A method for using an imaging system, the method comprising:
   injecting a patient with a contrast agent, wherein the injecting is performed without prior dosing of a patient by activation of the imaging system;
   activating the imaging system to dose a patient with radiation for acquiring low energy signal data and high energy signal data;
   obtaining a first material decomposed (MD) image of a first material basis and a second material decomposed (MD) image of a second material basis using the low energy signal data and the high energy signal data;
   inputting at least one of the first MD image or the second MD image into a guide filter for output of at least one noise reduced and cross-contamination reduced image; and
   outputting the noise reduced and cross-contamination reduced image on a display to an operator for observation and identification of a region of interest,
   wherein the guide filter is guided by a first guide image and a second guide image, the first guide image obtained by mixing the first MD image and the second MD image according to a first process, the second guide image is provided by mixing the first MD image and second MD image according to a second process and de-noising a mixed image resulting from the mixing according to the second process,
   further wherein the first guide image comprises a first de-noised cross-contaminated image provided by the first material basis and the second guide image comprises a second de-noised cross-contaminated image provided by the second material basis.

2. The method of claim 1, wherein according to the first process, negatively correlated noise of a first MD image and a second MD image is cancelled out.

3. The method of claim 1, wherein the first MD image is a water image and wherein the first guide image is a water image with cross contamination and lower noise than the first MD image.

4. The method of claim 1, wherein the second MD image is an iodine image and wherein the second guide image is an iodine image with cross contamination and lower noise than the second MD image.

5. A computed tomography (CT) imaging system comprising:
- an X-ray source;
- a detector having a plurality of detector elements that detect X-ray beams emitted from the X-ray source;
- wherein the CT imaging system comprises a processor-based system operative to:
  - acquire using the detector low energy signal data and high energy signal data;
  - obtain a first material decomposed (MD) image of a first material basis and a second material decomposed (MD) image of a second material basis using the low energy signal data and the high energy signal data; and
  - input at least one of the first or second MD image into a guide filter for output of at least one noise reduced and cross-contamination reduced image on a display to an operator for observation and identification of a region of interest,
  - wherein the guide filter is guided by a first guide image and a second guide image, the first guide image obtained by mixing the first MD image and the second MD image according to a first process, the second guide image obtained by mixing the first MD image and the second MD image according to a second process and de-noising a mixed image resulting from the mixing according to the second process,
  - further wherein the first guide image comprises a first de-noised cross-contaminated image provided by the first material basis and the second guide image comprises a second de-noised cross-contaminated image provided by the second material basis.

6. The CT imaging system of claim 5, wherein according to the first process, negatively correlated noise of a first MD image and a second MD image is cancelled out.

7. The CT imaging system of claim 5, wherein according to the second process, negatively correlated noise of a first MD image and a second MD image is not canceled out.

* * * * *